(12) United States Patent
Pu et al.

(10) Patent No.: US 7,813,016 B2
(45) Date of Patent: Oct. 12, 2010

(54) METHOD OF NONLINEAR HARMONIC HOLOGRAPHY

(75) Inventors: Ye Pu, Pasadena, CA (US); Demetri Psaltis, St-Sulpice (CH)

(73) Assignee: California Institute of Technology, Pasadena, CA (US)

( * ) Notice: Subject to any disclaimer, the term of this patent is extended or adjusted under 35 U.S.C. 154(b) by 351 days.

(21) Appl. No.: 11/944,068

(22) Filed: Nov. 21, 2007

(65) Prior Publication Data

US 2009/0067018 A1    Mar. 12, 2009

Related U.S. Application Data

(60) Provisional application No. 60/860,437, filed on Nov. 21, 2006.

(51) Int. Cl.
*G03H 1/02* (2006.01)
*G03H 1/00* (2006.01)

(52) U.S. Cl. .................................. 359/3; 359/35; 430/1

(58) Field of Classification Search .................. 359/3, 359/1, 35; 356/317; 430/1
See application file for complete search history.

(56) References Cited

U.S. PATENT DOCUMENTS

| | | | |
|---|---|---|---|
| 6,624,915 B1 * | 9/2003 | Kirkpatrick et al. ............. | 359/3 |
| 7,009,700 B2 * | 3/2006 | Dubois et al. ................ | 356/317 |
| 2005/0025422 A1 | 2/2005 | Magnusson et al. | |
| 2005/0186565 A1* | 8/2005 | Malak ............................ | 435/5 |
| 2005/0267345 A1* | 12/2005 | Korgel et al. ................ | 600/317 |

OTHER PUBLICATIONS

International Search Report for International Application No. PCT/US2007/085409, filed Nov. 21, 2007, Report completed Oct. 7, 2008, mailed Oct. 10, 2008, 2 pgs.
International Search Report for International Application No. PCT/US2007/085409, filed Nov. 21, 2007, Report completed Oct. 7, 2008, mailed Oct. 10, 2008, 2 pgs.
Akerman et al., "Nanocrystal targeting in vivo", PNAS, Oct. 1, 2002, vol. 99, No. 20, pp. 12617-12621.
Alivisatos, "The use of nanocrystals in biological detection", Nature Biotechnology, Jan. 2004, vol. 22, No. 1, pp. 47-52.
Andreoni et al., "Holographic properties of the second-harmonic cross correlation of object and reference optical wave fields", J. Opt. Soc. Am., Jun. 2000, vol. 17, No. 6, pp. 966-972.

(Continued)

*Primary Examiner*—Audrey Y Chang
(74) *Attorney, Agent, or Firm*—Kauth, Pomeroy, Peck & Bailey LLP (57) ABSTRACT

A harmonic holography ($H^2$) technique and system that combines holography and nonlinear optics that enables holographic recording of 3D images with femtosecond framing time are provided. The $H^2$ technique records holograms with second harmonic (SH) signals scattered off specialized nanocrystals that are functionalized to label specific protein or other biomolecules in a living organism. The capability of generating second harmonic radiations is specific to materials with noncentrosymmetric crystalline structures only, and $\chi^{(2)}$ vanishes for all other types of materials. Therefore, a sharp contrast is formed when particles of noncentrosymmetric structures are dispersed in a medium of other species, pumped at a fundamental frequency, and imaged at the second harmonic frequency. The new scheme described herein provides a sound basis for a new type of contrast microscopy with enormous potential in molecular biomedical imaging.

35 Claims, 9 Drawing Sheets

OTHER PUBLICATIONS

Bastiaens et al., "Fluorescence lifetime imaging microscopy: spatial resolution of biochemical processes in the cell", trends in Cell Bioloby, Feb. 1999, vol. 9, pp. 48-52.

Brauns et al., "Complex Local Dynamics in DNA on the Picosecond and Nanosecond Time Scales", Physical Review Letters; Apr. 15, 2002, vol. 88, No. 15, pp. 158101-1 thru 158101-4.

Callender et al., "Fast Events in Protein Folding: The Time Evolution of Primary Processes", Annu. Rev. Phys. Chem, 1998, vol. 49, pp. 173-202.

Chalfie et al., "Green Fluorescent Protein as a Marker for Gene Expression", Science, Feb. 11, 1994, vol. 263, pp. 802-805.

Cheatham, III, "Simulation and Modeling of nucleic acid structure, dynamics and interactions", Current Opinion in Structural Biology, 2004, vol. 14, pp. 360-367.

Cuche et al., "Simultaneous amplitude-contrast and quantitative phase-contrast microscopy by numerical reconstruction of Fresnel off-axis holograms", Applied Optics, Dec. 1, 1999, vol. 38, No. 34, pp. 6994-7001.

Dobson, "Protein folding and misfolding", Nature, Dec. 18-25, 2003, vol. 426, pp. 884-890.

Dubois et al., "Improved three-dimensional imaging with a digital holography microscope with a source of partial spatial coherence", Applied Optics, Dec. 1, 1999, vol. 38, No. 34, pp. 7085-7094.

Gabor, "A New Microscopic Principle", Nature, May 15, 1948, No. 4098, pp. 777-778.

Gerlich et al., "4D imaging to assay complex dynamics in live specimens", Reviews, Sep. 2003, pp. S14-S19.

Gilmanshin et al., "Fast events in protein folding: Relaxation dynamics of secondary and tertiary structure in native apomyoglobin", Proc. Natl. Acad. Sci. USA, Apr. 1997, vol. 94, pp. 3709-3713.

Jaiswal et al., "Use of quantum dots for live cell imaging", Nature Methods, Oct. 2004, vol. 1, No. 1, pp. 73-78.

Jares-Erijman et al., "FRET Imaging", Focus on Optical Imaging, Nature Biotechnology, Nov. 2003, vol. 21, No. 11, pp. 1387-1395.

Krenn et al., "Squeezing the Optical Near-Field Zone by Plasmon Coupling of Metallic Nanoparticles", Physical Review Letters, Mar. 22, 1999, vol. 82, No. 12, pp. 2590-2593.

Kubelka et al., "The protein folding 'speed limit'", Current Opinion in Structural Biology, 2004, vol. 14, pp. 76-88.

Leith et al., "Microscopy of Wavefront Reconstruction", Journal of the Optical Society of America, Aug. 1965, vol. 55, No. 8, pp. 981-986.

Leith et al., "Wavefront Reconstruction with Diffused Illumination and Three-Dimensional Objects", Journal of the Optical Society of America, Nov. 1964, vol. 54, No. 11, pp. 1295-1301.

Lichtman et al., "Fluorescence microscopy", Nature Methods, Dec. 2005, vol. 2, No. 12, pp. 910-919.

Maier et al., "Optical pulse propagation in metal nanoparticle chain waveguides", Physical Review, 2003, vol. B67, pp. 205402-1 thru 205402-5.

Maletic-Savatic et al., "Rapid Dendritic Morphogenesis in CA1 Hippocampal Dendrites Induced by Synaptic Activity", Science, Mar. 19, 1999, vol. 283, pp. 1923-1927.

Marquet et al., "Digital holographic microscopy: a noninvasive contrast imaging technique allowing quantitative visulation of living cells with subwavelength axial accuracy", Optics Letters, Mar. 1, 2005, vol. 30, No. 5, pp. 468-470.

Miccio et al., "Direct full compensation of the aberrations in quantitative phase microscopy of thin objects by a single digital hologram", Applied Physics Letters, 2007, vol. 90, pp. 041104-1 thru 041104-3.

Michalet et al., "Quantum Dots for Live Cells, in Vivo Imaging and Diagnostics", Science, Jan. 28, 2005, vol. 307, pp. 538-544.

Michalet et al., "The Power and Prospects of Fluorescence Microscopies and Spectroscopies", Annu. Rev. Biophys. Biomol. Struct, 2003, vol. 32, pp. 161-182.

Millar, "Fluorescence studies of DNA and RNA structure and dynamics", Current Opinion in Structural Biology, 1996, vol. 6, pp. 322-326.

Miyawaki et al., "Dynamic and quantitative $Ca^{2+}$ measurements using improved cameleons", Proc. Natl. Acad. Sci. USA, Mar. 1999, vol. 96, pp. 2135-2140.

Pedrini et al., "Aberration compensation in digital holographic reconstruction of microscopic objects", Journal of Modern Optics, 2001, vol. 48, No. 6, pp. 1035-1041.

Pollock et al, "Using GFP in FRET-based applications", trends in Cell Biology, Feb. 1999, vol. 9, pp. 57-60.

Pu et al., "Four-dimensional dynamic flow measurement by holographic particle image velocimetry", Applied Optics, Dec. 20, 2005, vol. 44, No. 36, pp. 7697-7708.

Pu et al., "Intrinsic aberrations due to Mie scattering in particle holography", J. Opt. Soc. Am, Oct. 2003, vol. 20, No. 10, pp. 1920-1932.

Schnars et al., "Direct recording of holograms by a CCD targtet and numerical reconstruction", Applied Optics, Jan. 10, 1994, vol. 33, No. 2, pp. 179-181.

Shi et al., "Rapid Spine Delivery and Redistribution of AMPA Receptors After Synaptic NMDA Receptor Activation", Science, Jun. 11, 1999, vol. 284, pp. 1811-1816.

Suhling et al., "Time-resolved fluorescence microscopy", Photochem. Photobiol. Sci, 2005, vol. 4, pp. 13-22.

Toth et al., "Reconstruction of a Three-Dimensional Microscopic Sample Using Holographic Techniques", Applied Physics Letters, Jul. 1, 1968, vol. 13 No. 1, p. 7-10.

Trifonov et al., "Ultrafast Energy Transfer and Structural Dynamics in DNA", J. Phys. Chem, 2005, vol. 109, pp. 19490-19495.

Whitesides, "The 'right' size in nanobiotechnology", Nature Biotechnology, Oct. 2003, vol. 21, No. 10, pp. 1161-1165.

Williams et al., "Fast Events in Protein Folding: Helix Melting and Formation in a Small Peptide", Biochemistry, 1996 vol. 35, pp. 691-697.

Xu et al., "Tracking particles in four dimensions with in-line holographic microscopy", Optics Letters, Feb. 1, 2003, vol. 28, No. 3, pp. 164-166.

Yamaguchi et al., "Phase-shifting digital holography", Optics Letters, Aug. 15, 1997, vol. 22, No. 16, pp. 1268-1270.

Zhang et al., "Three-dimensional microscopy with phase-shifting digital holography", Optics Letters, Aug. 1, 1998, vol. 23, No. 15, pp. 1221-1223.

Zipfel et al., "Nonlinear magic: multiphoton microscopy in the biosciences", Nature Biotechnology, Nov. 2003, vol. 21, No. 11, pp. 1369-1377.

* cited by examiner

METHOD OF NONLINEAR HARMONIC HOLOGRAPHY

CROSS-REFERENCE TO RELATED APPLICATIONS

The current application claims priority to U.S. Provisional Application No. 60/860,437, filed Nov. 21, 2006, the disclosure of which is incorporated herein by reference.

STATEMENT OF FEDERAL RIGHTS

The U.S. Government has certain rights in this invention pursuant to Grant No. HR0011-04-1-0032 awarded by DARPA.

FIELD OF THE INVENTION

The current invention is directed to a harmonic holography ($H^2$) technique and system that combines holography and nonlinear optics that enables holographic recording of 3D images with femtosecond framing time.

BACKGROUND OF THE INVENTION

Biological cells and tissues feature extremely complex three-dimensional (3D) structures spanning a large range of length scale. Living organisms are also very dynamic; molecular processes take place in a timescale covering over 15 orders of magnitudes while the organisms move and metabolize. For example, molecular processes such as protein, DNA, and RNA conformation changes take place in a timescale ranging from 100 fs to 100 s. (For discussion, see, e.g., Whitesides, G. M., Nat. Biotechnol. 21, 1161-1165 (2003); Williams, S. et al., Biochemistry 35, 691-697 (1996); Gilmanshin, R., et al., Proc. Natl. Acad. Sci. U.S.A. 94, 3709-3713 (1997); Callender, R. H., et al., Annual Review of Physical Chemistry 49, 173-202 (1998); Trifonov, A. et al., Journal of Physical Chemistry B 109, 19490-19495 (2005); Cheatham, T. E., Curr. Opin. Struct. Biol. 14, 360-367 (2004); Millar, D. P., Curr. Opin. Struct. Biol. 6, 322-326 (1996); and Brauns, E. B., et al., Physical Review Letters 88 (2002), the disclosures of which are incorporated herein by reference.) The understanding of these processes not only has fundamental biological significance, but also will enable the treatment of a host of human diseases. Essentially, probing these processes requires a "whole-field" technique, which means taking 3D microscopic pictures in a rapid succession with high sensitivity and specificity without scanning, i.e. a four-dimensional (4D) microscope is needed.

Since holography was invented 60 years ago, an aberration-free, three-dimensional microscope has long been sought. (See, e.g., D. Gabor, "A new microscopic principle", Nature 161, 777-778 (1948), the disclosure of which is incorporated herein by reference.) In fact, soon after Leith and Upatniek demonstrated the first 3D image by holography, holographic microscopy was proposed. With the recent advent of digital holography, holographic 3D microscopy received renewed and rapidly increasing attention. (E. N. Leith and Upatniek J., J. Opt. Soc. Am. 54, 1295-& (1964); E. N. Leith, et al., J. Opt. Soc. Am. 55, 981-& (1965); U. Schnars and W. Juptner, Appl. Opt. 33, 179-181 (1994); I. Yamaguchi and T. Zhang, Opt. Lett. 22, 1268-1270 (1997); E. Cuche, et al., Appl. Opt. 38, 6994-7001 (1999); F. Dubois, et al., Appl. Opt. 38, 7085-7094 (1999); P. Marquet, et al., Opt. Lett. 30, 468-470 (2005); L. Miccio, et al., Appl. Phys. Lett. 90, 3 (2007); L. Toth and S. A. Collins, Appl. Phys. Lett. 13, 7-& (1968); W. Xu, et al., Opt. Lett. 28, 164-166 (2003); and T. Zhang and I. Yamaguchi, Opt. Lett. 23, 1221-1223 (1998), the disclosure of which are incorporated herein by reference.) Holography is a "whole-field" technique, which means recording all 3D pixels simultaneously in one laser shot without scanning, an extremely valuable asset for biomedical imaging. When combined with modern high-repetition rate pulsed laser and fast imaging devices, a time sequence of consecutive 3D images can be captured, forming a 4D microscope. Indeed, successful 4D holographic imaging has been achieved recently in the context of fluid velocity measurement. (See, e.g., Y. Pu and H. Meng, Appl. Opt. 44, 7697-7708 (2005), the disclosure of which is incorporated herein by reference.)

Despite the technical advancements, holographic microscopes are not widely deployed in biomedical research because of the lack of specificity. In a microscopic setting with biological samples, holography alone suffers severe background scatterings from irrelevant cell structures. A holographic microscope would capture all scattering entities in the viewing field faithfully, but indiscriminately. On the other hand, the signals of interest (often from small nanostructures like protein molecules) are usually very weak and buried in the strong ambient scatterings from much larger organelles.

A key to achieve the specificity required for molecular biomedical imaging is to create a contrast between the useful signal and the ambient scatterings. Contrast imaging is routinely achieved through tagging the molecule or nanostructure of interest with fluorescent agents, such as fluorescent dyes, green fluorescent proteins (GFPs), and quantum dots (QDs). By converting the light signal into a different frequency, the unwanted ambient scattering can be easily removed with proper optical filters.

Recent advances in fluorescence microscopy have profoundly changed how cell and molecular biology is studied in almost every aspect. (See, e.g., Lichtman, J. W. & Conchelo, J. A., Nat. Methods 2, 910-919 (2005); Michalet, X. et al., Annu. Rev. Biophys. Biomolec. Struct. 32, 161-182 (2003); Jares-Erijman, E. A. & Jovin, T. M., Nat. Biotechnol. 21, 1387-1395 (2003); Bastiaens, P. I. H. & Squire, A., Trends Cell Biol. 9, 48-52 (1999); Suhling, K., et al., Photochem. Photobiol. Sci. 4, 13-22 (2005); Chalfie, M., et al., Science 263, 802-805 (1994); Pollok, B. A. & Heim, R., Trends Cell Biol. 9, 57-60 (1999); Jaiswal, J. K., et al., Nat. Methods 1, 73-78 (2004); Michalet, X. et al., Science 307, 538-544 (2005); Zipfel., W. R., et al., Nature Biotechnol. 21, 1368-1376 (2003); Shi, S. H. et al., Science 284, 1811-1816 (1999); Maletic-Savatic, M., et al., Science 283, 1923-1927 (1999); Miyawaki, A., et al., Proc. Natl. Acad. Sci. U.S.A. 96, 2135-2140 (1999); Akerman, M. E., et al., Proc. Natl. Acad. Sci. U.S.A. 99, 12617-12621 (2002); and Alivisatos, P., Nat. Biotechnol. 22, 47-52 (2004), the disclosures of which are incorporated herein by reference.) However, as an incoherent optical process, fluorescence lacks the capability of 3D representation. Should 3D information be required, point-scanning technique has to be performed over the entire volume of interest. The elapsed time for the scanning (i.e. the 3D framing time) is usually in the order of seconds to minutes, which severely constrains the use of this technique. Attempts to extend fluorescence microscopy into three spatial dimensions over time (4D microscopy) are thus incapable of capturing dynamic events. (See, e.g., D. Gerlich and J. Ellenberg, Nat. Cell Biol. 5, S14-S19 (2003), the disclosure of which is incorporated herein by reference.)

Accordingly, a new holographic imaging methodology and system is needed that allows for dynamic 4D imaging with high contrast and ample spatial and temporal resolution.

SUMMARY OF THE INVENTION

The current invention is directed to a harmonic holography ($H^2$) technique and system that combines holography and nonlinear optics that enables holographic recording of 3D images with femtosecond framing time.

In one embodiment, the harmonic holograph system and method includes the following components/steps: a first optical splitter for separating said an optical pulse excitation an reference pulses; a sample including a target of interest having a nanoparticle incorporated therein for generating one coherent nonlinear optical emission when radiated; an optical filter for blocking all emissions from said sample except nonlinear emissions; a nonlinear homodyne reference generator, such as a frequency doubler, for converting the reference pulse into one coherent nonlinear reference pulse; a second optical splitter for recombining the split pulses into one holographic signal; and a detector for recording the holographic signal. In such an embodiment either multiple or a single excitation pulse may be used.

In another embodiment, the nonlinear holographic imaging system and method of the invention further includes a computer algorithm to process the hologram recorded on the detector and reconstruct the images of said nanocrystals.

In still another embodiment, the nonlinear holographic imaging system and method of the invention further includes obtaining images of the at least one nanocrystal on multiple planes.

In yet another embodiment, the nonlinear holographic imaging system and method of the invention further includes repeating the recording over time to obtain dynamic imaging of a process of interest.

In still yet another embodiment, the nanoparticle used in the nonlinear holographic imaging system and method of the invention is a nanocrystal. In such an embodiment the nanocrystal may be selected from the group consisting of $BaTiO_3$, SiC, ZnO, ZnS, ZnSe, ZnTe, CdS, CdSe, CdTe, GaAs, GaSb, GaP, GaN, InSb, $LiNbO_3$, $KNbO_3$, $KTiOPO_4$, $Fe(IO_3)_3$, Au, Ag, N-(4-nitrophenyl)-(L)-prolinol (NPP), 4-Nitroaniline, 2-Methyl-4-nitroaniline (MNA), and 3-Methyl-4-methoxy-4'-nitrostilbene. Further in such an embodiment the nanocrystal is functionalized to attach to a specific target of interest.

In still yet another embodiment, the target of interest of the nonlinear holographic imaging system and method of the invention is a biomolecule selected from the group consisting of proteins, polypeptides, DNAs, RNAs, nucleotides, neocleosides, lipids, Ligands, receptors, and ion channels. In another such embodiment, the target of interest may be a microfluidic device. Regardless the sample containing the target of interest may be a three dimensional media.

In still yet another embodiment, the nonlinear holographic imaging system and method of the invention further includes a plurality of additional optical conditioning devices selected from the group consisting of mirrors, negative lenses, positive lenses, aspheric lenses, filters, optical splitters, and objectives.

In still yet another embodiment, the nonlinear emission of the nonlinear holographic imaging system and method of the invention is produced by a process selected from the group consisting of second harmonic generation, third harmonic generation, fourth harmonic generation, sum frequency generation, difference frequency generation, optical parametric down conversion, stimulated Raman scattering, coherent anti-Stokes Raman scattering, and surface-enhanced Raman scattering.

In still yet another embodiment, the nonlinear holographic imaging system and method of the invention, uses at least two metal nanoparticles incorporated into the target of interest, such that when illuminated by the pulses from the excitation source the at least two metal nanoparticles produce different absorption spectrum transmissions as a result of a collective plasmon resonance phenomenon dependent on the relative distance between the at least two metal nanoparticles. In such an embodiment, the transmissions from the sample are recombined into a holographic signal and all holographic signals except the holographic signal at a frequency of interest are blocked. In one related embodiment, the relative distance between the at least two metal nanoparticles changes to produce at least two different absorption spectrum and the detector records the holographic signal of the two states in rapid succession. In such an embodiment, a computer algorithm maybe used to calculate the image of absorption difference between said first and second state at said frequency of interest from said holographic signal and obtain difference images between the two states on multiple planes. The recording may also be repeated over time to obtain dynamic imaging of a process of interest.

In still yet another embodiment, the metal nanoparticles of the nonlinear holographic imaging system and method of the invention are selected from the group consisting of Au, Ag, Al, Cu, Pd, and Pt. In such an embodiment, the two metal nanoparticles may be functionalized to attach to a specific target of interest.

BRIEF DESCRIPTION OF THE DRAWINGS

The description will be more fully understood with reference to the following figures and data graphs, which are presented as exemplary embodiments of the invention and should not be construed as a complete recitation of the scope of the invention, wherein.

DETAILED DESCRIPTION OF THE INVENTION

The process of second harmonic generation (SHG) has a unique property of forming sharp optical contrast between noncentrosymmetric crystalline materials and other types of materials, which is a highly valuable asset for contrast microscopy. The coherent signal obtained through SHG also allows for the recording of holograms at high spatial and temporal resolution, enabling whole-field four-dimensional microscopy for highly dynamic micro- and nano-systems.

The current invention is directed to a harmonic holography technique and system, referred to hereinafter as $H^2$, that combines holography and nonlinear optics that enables holographic recording of 3D images with femtosecond framing time. Briefly, $H^2$ records holograms with between a reference and second harmonic (SH) signals scattered from specialized nanocrystals that are functionalized to label specific protein or other biomolecules in a living organism. When a nanocrystal of a noncentrosymmetric structure (a crystal structure that lacks an inversion center) is under the excitation of an intense optical field $E(\omega)$, the polarization $P(\omega)$ of the nanocrystal is described by a Taylor expansion series:

$$P(\omega) = \chi^{(1)} \cdot E(\omega) + \chi^{(2)} \cdot E(\omega) \cdot E(\omega) + \chi^{(3)} \cdot E(\omega) \cdot E(\omega) \cdot E(\omega) + \ldots, \quad (\text{Eq. 1})$$

where the coefficient $\chi^{(n)}$ is the nth-order susceptibilities of the crystal material. The second-order response, $\chi^{(2)} \cdot E \cdot E$, gives rise to a radiation at exactly twice the frequency of the pumping field. The capability of generating second harmonic radiations is specific to materials with noncentrosymmetric crystalline structures only, and $\chi^{(2)}$ vanishes for all other types of materials. Therefore, a sharp contrast is formed when particles of noncentrosymmetric structures are dispersed in a medium of other species, pumped at a fundamental frequency, and imaged at the second harmonic frequency. Specifically, with only a few exceptions, biological cells and tissues are incapable of generating endogenous second harmonic emissions. Therefore, the new scheme described here provides a sound basis for a new type of contrast microscopy with enormous potential in molecular biomedical imaging.

SHG is an ultrafast process, permitting the probe of dynamics at femtosecond level. As a result, the holography of the current invention is also capable of recording 3D images in a single laser shot allowing for dynamic, four-dimensional (4D) holographic recording for microparticles embedded in 3D media. Apart from the capability of 3D representation and femtosecond response time, the use of SH generating nanocrystals instead of fluorescent dies also has many other advantages, including no photo-bleaching, no signal saturation, no background auto-fluorescence, and higher signal-to-noise ratio. Finally, in contrast to fluorescence, a second harmonic signal is coherent, enabling holography with contrast at doubled spatial resolution.

Figure 1:
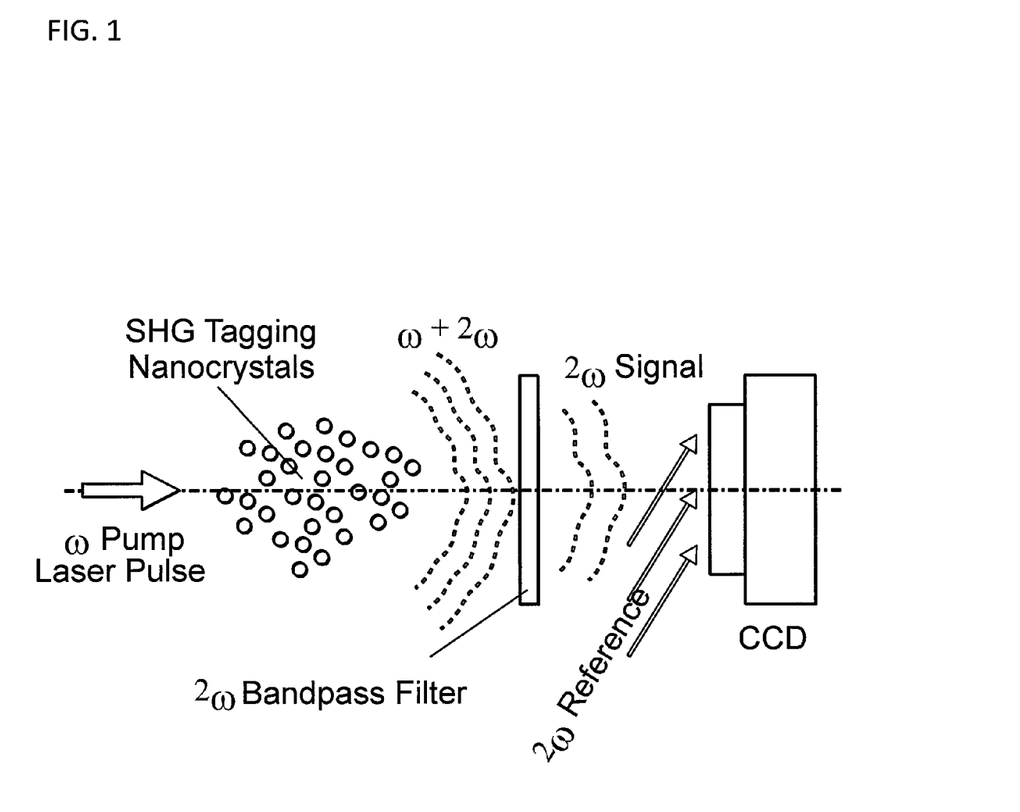
FIG. 1 provides a schematic of the principle of operation of the harmonic holography technique in accordance with the current invention.

FIG. 1 illustrates the principle of $H^2$. In this scheme, an intense laser pulse at frequency $\omega$ is delivered to a group of second harmonic generating nanoparticles, which are tagged to specific parts of the system under investigation. Although any nanoparticle, organic or inorganic, having no inversion symmetry and thus capable of generating a second harmonic emission when excited may be used, exemplary nanoparticles include nanocrystals, such as, for example, $BaTiO_3$, SiC, ZnO, ZnS, ZnSe, ZnTe, CdS, CdSe, CdTe, GaAs, GaSb, GaP, GaN, InSb, $LiNbO_3$, $KNbO_3$, $KTiOPO_4$, $Fe(IO_3)_3$, N-(4-nitrophenyl)-(L)-prolinol (NPP), 4-Nitroaniline, 2-Methyl-4-nitroaniline (MNA), or 3-Methyl-4-methoxy-4'-nitrostilbene.

The nanoparticles emit scattering signals at both the fundamental ($\omega$) and second harmonic ($2\omega$) frequencies. A bandpass filter centered at $2\omega$ rejects the pumping and scattered light at frequency $\omega$ but transmit the $2\omega$ signal to the charge coupled device (CCD) sensor. A reference beam at frequency $2\omega$, independently generated from the same pump laser pulse, is also delivered to the CCD sensor and a hologram is thus formed. More specifically, the input femtosecond laser pulses are split into pump and reference pulses at the first beamsplitter (BS1), and the SH signals collected by the objective are then recombined with the reference obtained from a separate SH generator at the second beamsplitter (BS2) to form a hologram at the CCD sensor. Accordingly, structures that are not capable of generating second harmonic signals only scatter at $\omega$ and will not be recorded on the hologram. From the captured SH hologram a stack of image planes (not shown) can be reconstructed to from the 3D images of the nanocrystals. In the figure the mirrors are labeled M1 and M2 and the lenses are labeled L1 and L2. It should be understood that while a single optical arrangement is provided in FIG. 1, this is only a representative example of a system capable of obtaining second harmonic holographic images in accordance with the current invention.

Fast, 3D imaging presents a number of challenges. The second harmonic emissions from nanocrystals are usually extremely weak, often only a few photons per pulse. Furthermore, high numerical aperture (NA) lenses and objectives are often only optimized for one imaging plane, resulting in substantial aberrations when working with a volume of finite depth. In addition, fast image sensors with small pixels required in $H^2$ are typically much noisier than slower ones with larger pixels. Therefore, in the abstract an implementation of $H^2$ in accordance with the current invention would seemingly encounter a serious signal to noise ratio (SNR) problem.

The holographic system in accordance with the current invention is able to address these issues simultaneously. First, objective aberrations can be numerically canceled or compensated in holography to obtain diffraction limited imaging performance. (See, e.g., A. Andreoni, et al., J. Opt. Soc. Am. B 17, 966-972 (2000), the disclosure of which is incorporated herein by reference.) Moreover, the reference used in holography serves as a coherent bias that is much higher than the device noise in the imaging sensor, leading to a shot noise-limited performance in the low photon count regime. (See, e.g., G. Pedrini, et al., J. Mod. Opt. 48, 1035-1041 (2001), the disclosure of which is incorporated herein by reference.)

Figure 2:
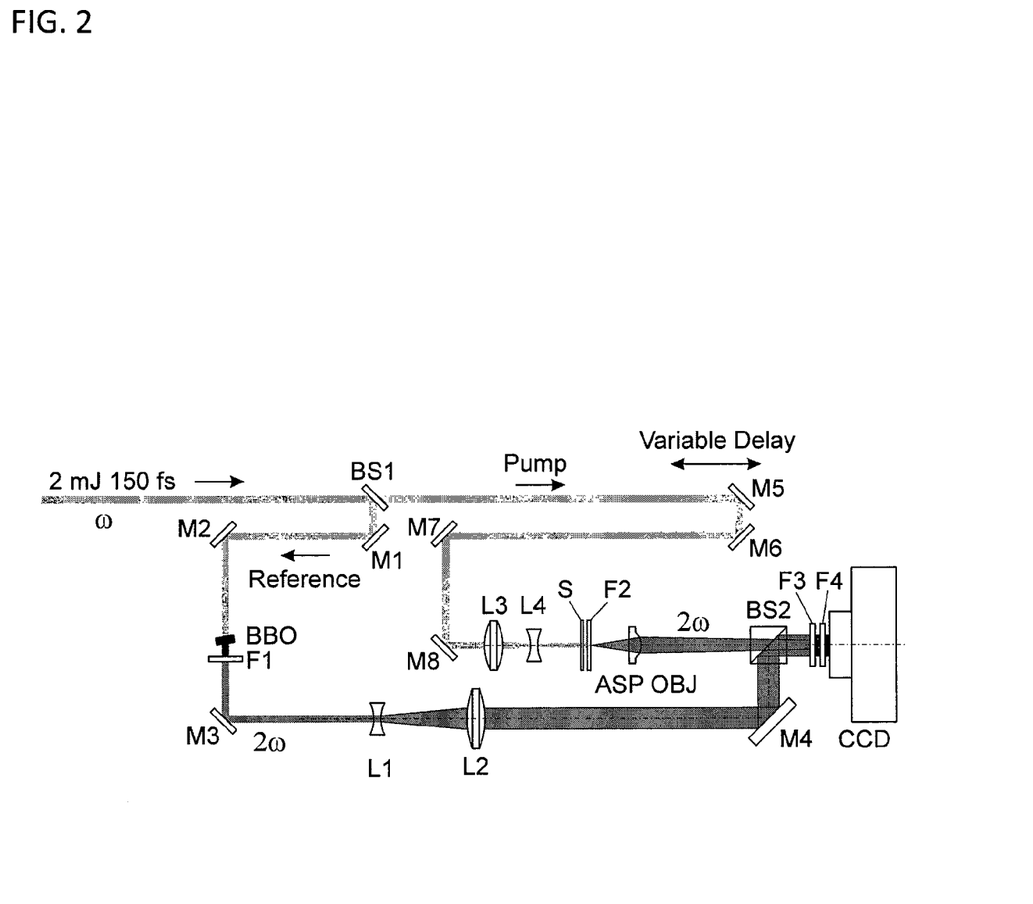
FIG. 2 provides a detailed schematic of an exemplary harmonic holography instrument in accordance with the current invention.

Turning to the structure of the harmonic holography device, although a number of optical arrangements are possible, FIG. 2 shows an exemplary instrumentation setup for the $H^2$ system. As shown in the figure, femtosecond laser pulses (810 nm wavelength in the current example) are first split into two branches by a first beamsplitter (BS1). Energy is then delivered to a sample (S) containing the second harmonic generating nanoparticles. The energy delivered to the sample and pump intensity at the sample site may be adjusted to suit the sample and nanocrystals to be used. In one exemplary embodiment an energy of from approximately 1 to 2 mJ can be used to generate a pump intensity at the sample of on the order of $1 \times 10^{11}$ W/cm$^2$. After the pump energy at the fundamental frequency is rejected, the weak SH radiations from the nanocrystals (the object wave) are collected by an aspheric lens (N.A.=0.5 in the current example) at appropriate magnification, (25× in the current example). The rest of the pulse energy is then sent to a frequency doubler (beta barium borate or BBO crystal in the current example), to obtain the reference SH wave. The object and reference waves are then combined at a second beamsplitter (BS2), and the interference patterns are captured by a CCD camera. The optical path lengths of the two SH waves are carefully matched by the variable delay line.

Other optional optical components may also be used to condition and redirect the light to ensure optimal delivery to the sample and detector, such as, in the current example, mirrors (M1 to M7), negative lenses (L1 & L2), positive lenses (L3 & L4), filters (F1 to F4), and an aspheric objective (ASP OBJ). Although a specific optical arrangement is shown in FIG. 2, it should be understood that other combinations of optics may be used to provide the same second harmonic holography functionality.

Once the hologram is recorded the images of the sample can be numerically reconstructed. Among a number of possible reconstruction algorithms, one particular exemplary embodiment reconstructs numerically the electric field of the objective wave at the sample plane from the digital image captured by the CCD camera. In this example, the reference was introduced at near-zero angle with respect to the optical axis, and the hologram is treated as in-line. The reconstruction algorithm was essentially a convolution between the holographic image intensity and the system impulse function:

$$\Gamma(\xi,\eta,\zeta) = h(x,y) * g(x,y;\zeta), \quad (Eq.\ 2)$$

where $\Gamma(\xi,\eta,\zeta)$ is the reconstructed 3D image intensity at object coordinate $(\xi,\eta,\zeta)$, $h(x,y)$ is the intensity of the holographic image captured from the CCD at hologram coordinate $(x,y)$, and $g(x,y;\zeta)$ is the system impulse function at object coordinate $\zeta$ along the optical axis. (For discussion see, U. Schnars and W. P. O. Juptner, Meas. Sci. Technol. 13, R85-R101 (2002), the disclosure of which is incorporated herein by reference.) Images of nanocrystals dispersed in 3D space, therefore, can be extracted from a single hologram through appropriate $\zeta$.

This convolution was implemented as a sequence of fast Fourier transforms (FFTs) and inverse FFTs. In the current configuration, the aspheric objective was not designed to accommodate the thick filter F2 (1.7 mm thickness in the current example) which causes significant spherical aberration in the image. To compensate for such aberrations, the impulse function $g(x,y;\zeta)$ can be computationally generated through ray tracing with precise design parameters published by the manufacturer. With this approach, it is possible to completely cancel the aberration effect and obtain a reconstructed image with near diffraction-Limited performance.

Although the above implementation of the $H^2$ technique provides data for second harmonic signals, it should be understood that the $H^2$ technique can be extended to use any coherent nonlinear process with proper homodyne reference generator. These nonlinear processes include, but are not limited to, third harmonic generation (THG), fourth harmonic generation (FHG), sum frequency generation (SFG), difference frequency generation (DFG), optical parametric down conversion (SPDC), stimulated Raman scattering, coherent anti-Stokes Raman scattering (CARS), and surface-enhanced Raman scattering (SERS).

Figure 3A:
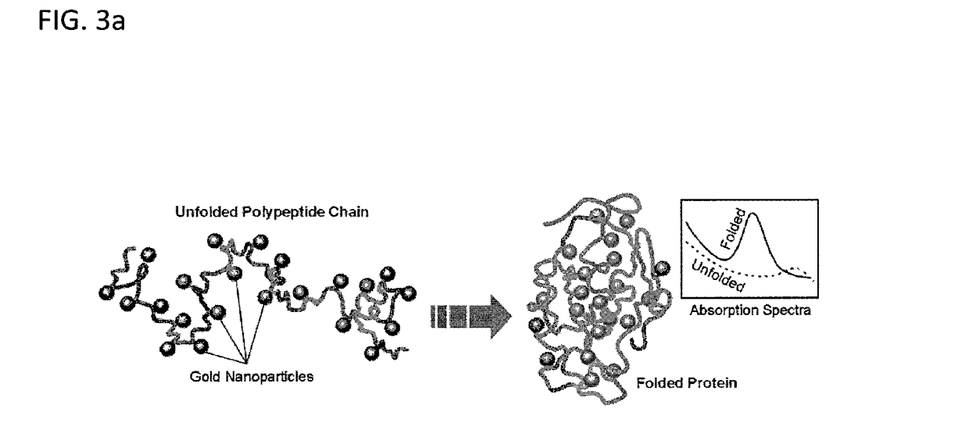
FIG. 3a provides a schematic of an exemplary application of the harmonic holography instrument in accordance with the current invention for use in imaging protein folding events.
Figure 3B:
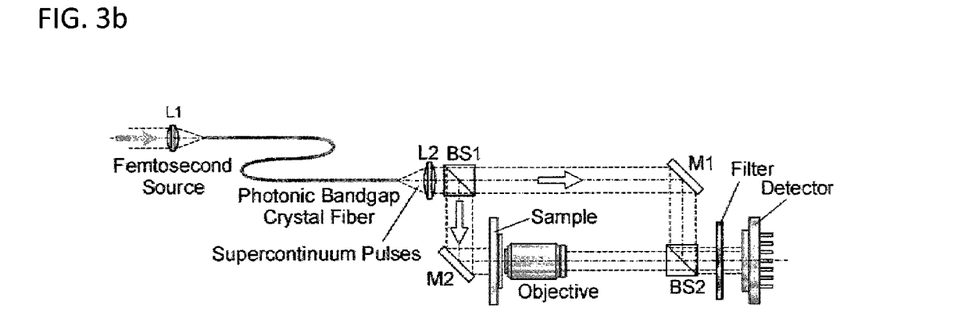
FIG. 3b provides a schematic of an exemplary harmonic holography instrument in accordance with the current invention for use in imaging protein folding events.

In addition, the nonlinear optical imaging technique of the current invention may also be extended for imaging dynamic biological processes, such as protein and genome activity, through linear optical processes. A particular example of such a technique using surface plasmon resonance of metal nanoparticles is shown in FIGS. 3a and 3b, where 1-2 nm Au nanoparticles are used to stain the full chain of a polypeptide with high density. As shown in FIG. 3a, because of the extremely small size of the Au nanoparticles, no plasmon resonance will be observed when the protein is unfolded. When the protein folds into a complex 3D structure, the Au nanoparticles are forced into a compact aggregate, where the collective surface plasmon shows distinct nonlocal resonance signatures. The inset sketches the optical spectra when the polypeptide chain transits form unfolded (dashed line) to folded state (solid line). While similar effects have been observed with Au NP-adsorbed DNA molecules, (see, e.g., Storhoff, J. J. et al. J. Am. Chem. Soc. 122, 4640-4650 (2000), the disclosure of which is incorporated herein by reference) the fast plasmon response bears enormous potential for revealing protein conformations at femtosecond level when imaged with holographic technique.

FIG. 3b illustrates a particular exemplary $H^2$ imaging system utilizing the spectral signature described above. The embodiment uses supercontinuum generated from a photonic crystal fiber under femtosecond pump as the light source. A band pass filter is used to pick up the signature spectra of the folded protein decorated with Au nanoparticles. As before, components of the optical system are labeled according to the following mirrors (M1 & M2), beamsplitter (BS1 & BS2), and lenses (L1 & L2).

Although many cellular components may also scatter light in this signature band and appear indistinguishable from the gold-labeled protein molecules, the new concept of temporal contrast can be used to achieve labeling specificity. Specifically, taking advantage of the ultrafast framing time of the $H^2$ technique, and the unique timescale in molecular conformations, the difference between two subsequent frames captured within such timescale reveals information highly specific to these molecular dynamics (For a further discussion, see, Dobson, C. M., Nature 426, 884-890 (2003); Kubelka, J., et al., Curr. Opin. Struct. Biol. 14, 76-88 (2004); Maier, S. A., et al., Physical Review B 67 (2003); and Krenn, J. R. et al., Physical Review Letters 82, 2590-2593 (1999), the disclosures of which are incorporated herein by reference).

EXAMPLE

To demonstrate the imaging potential of the $H^2$ technique, data was collected using an exemplary $H^2$ system with digital holographic recording of second harmonic signals up-converted from an ensemble of second harmonic generating nanocrystal clusters under femtosecond laser excitation. The results show that $H^2$ is uniquely suited for ultrafast four-dimensional contrast microscopy. The following section provides a summary of the system and data. It should be understood that this is merely provided as an exemplary embodiment and other arrangements of sources and optics may be created to provide the harmonic holography functionality of the current invention.

The instrumentation of the exemplary device used to collect the data presented herein is depicted in FIG. 2. As shown, femtosecond laser pulses of 2 mJ energy, 150 fs full width half maximum (FWHM) duration, and 810 nm wavelength (repetition rate 10 Hz) are split into a pump and a reference beam at a first beamsplitter (BS1). Approximately 1 mJ of the energy is delivered to the sample (S) containing randomly dispersed SHG imaging targets. After the boost in intensity through the reversed 3:1 telescope (L3 and L4), the pump intensity at the sample site is approximately $1 \times 10^{11}$ W/cm$^2$.

While the intense pump beam at the fundamental frequency is rejected by the filter (F2), the weak second harmonic radiations form the samples (the object wave) are picked up by the aspheric objective (N.A.=0.5) at a magnification of 25× (ABJ OBJ). The reference, independently frequency-doubled through a BBO crystal, meets and interferes with the signal at the second beamsplitter (BS2) to form the holograms that are captured by the CCD camera. The optical path lengths of the two second harmonic waves are carefully matched by the variable delay line.

Figure 4:
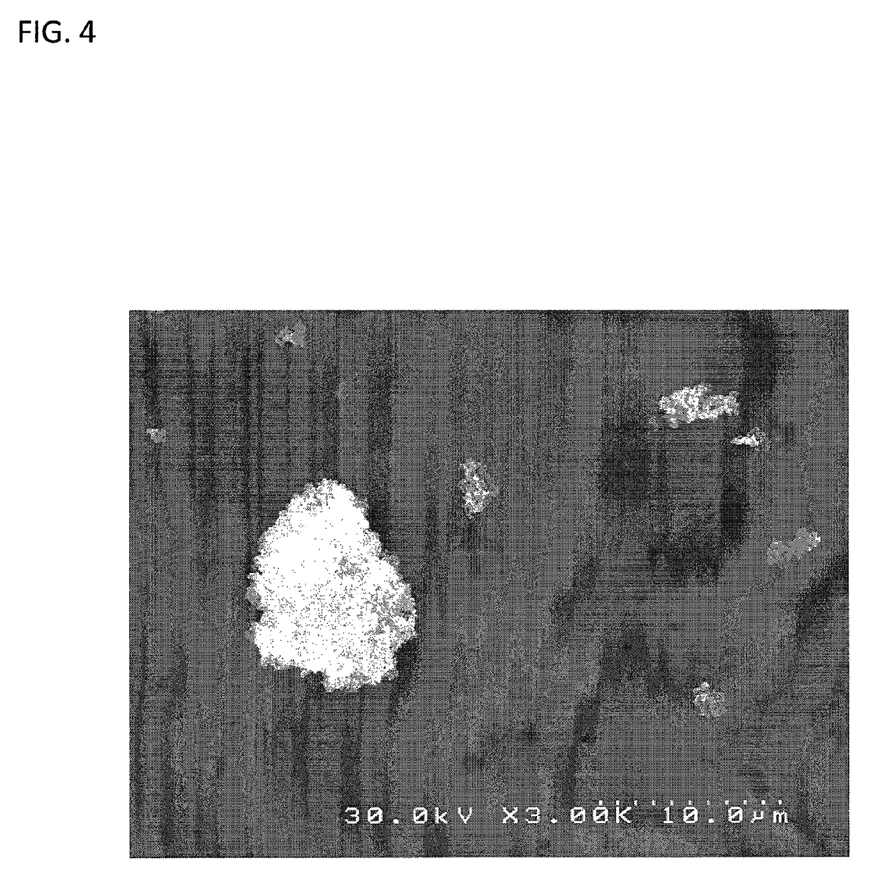
FIG. 4 provides photographic SEM data images of an exemplary sample for use with the harmonic holography instrument in accordance with the current invention.

In the current example, clusters of 100 nm $BaTiO_3$ nanocrystats were used as the imaging target. Although tetragonal phase $BaTiO_3$ has an excellent nonlinear coefficient $\chi(2)$, the unprocessed nanocrystals are in a centrosymmetric cubic crystal structure and are unable to produce second harmonic responses. To obtain tetragonal phase crystals, the nanocrystals are sintered at 1000° C. for one hour and rapidly cool them in deionized water. White the sintering converts the crystal structures into tetragonal phase crystals, large clusters result from such a process with a broad variation in size, as revealed by the scanning electronic microscopy (SEM) images shown in FIG. 4. For better control on the number density of particles, the larger clusters are collected through sedimentation and dispersed randomly on a microscope cover slip. Because of the "random phase-matching" condition, speckle-like, randomly located spots are expected within the extent of each cluster at the second harmonic frequency.

In the current embodiment, the position of the sample is adjustable. A "direct" (on-focus) image is captured when the reference is shut off and the sample is positioned at the imaging focal plane. A hologram, on the other hand, is obtained when the sample is moved off focus by a short distance (30 µm in this experiment) and the reference is turned on.

The camera used in the experiment was a thermal-electrically cooled CCD camera with 6.8 µm pixels and 7e- read noise. The quantum efficiency (QE) of the image sensor was approximately 50% at 400 nm wavelength. The digitization sensitivity of the camera was factory-calibrated to 3e- per digit. The camera was cooled down to 35° C. below the ambient temperature throughout the experiment, although the dark current does not play a significant role in the noise figure. The intensity of the hologram reference was set to at least 100 times stronger than the read noise of the CCD so that the read noise does not contribute significantly to the overall noise.

Figure 5:
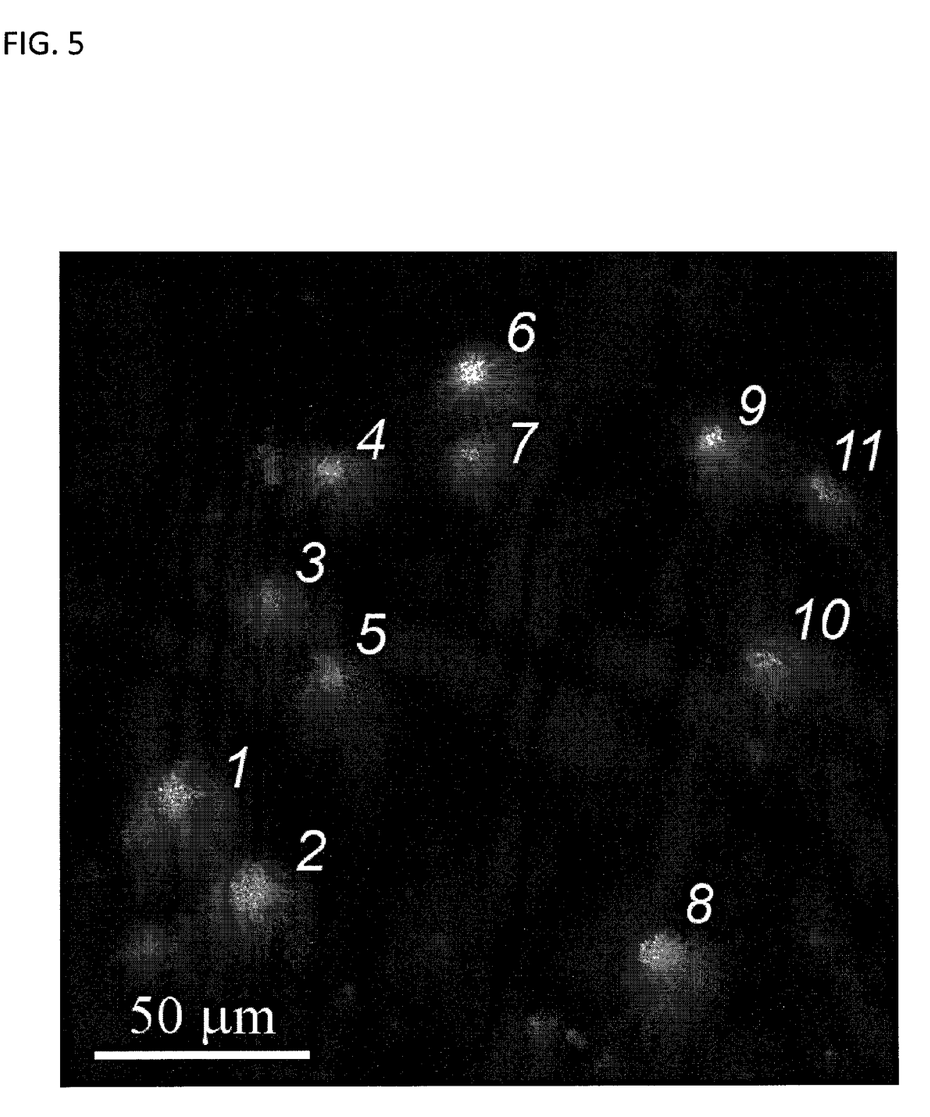
FIG. 5 provides photographic data images taken using an exemplary harmonic holography instrument in accordance with the current invention.

As indicated in previous sections, imaging with second harmonic signals often involve very low photon count. Thus an accurate estimate of signal levels for quantifying SNR becomes difficult because of the intensity fluctuations due to shot noise. Since the signal level is directly proportional to the number of pulses integrated, the signal intensity can be estimated as an integration of $n_1$ pulses through an image of $n_2$ pulses by $I_1=n_1 I_2/n_2$, where $n_2 \gg n_1$. An on-focus (direct) second harmonic image of the nanocrystal clusters is shown in FIG. 5. The image is acquired with an integration of 100 pulses and serves as an accurate measurement of signal intensity.

Figure 6:
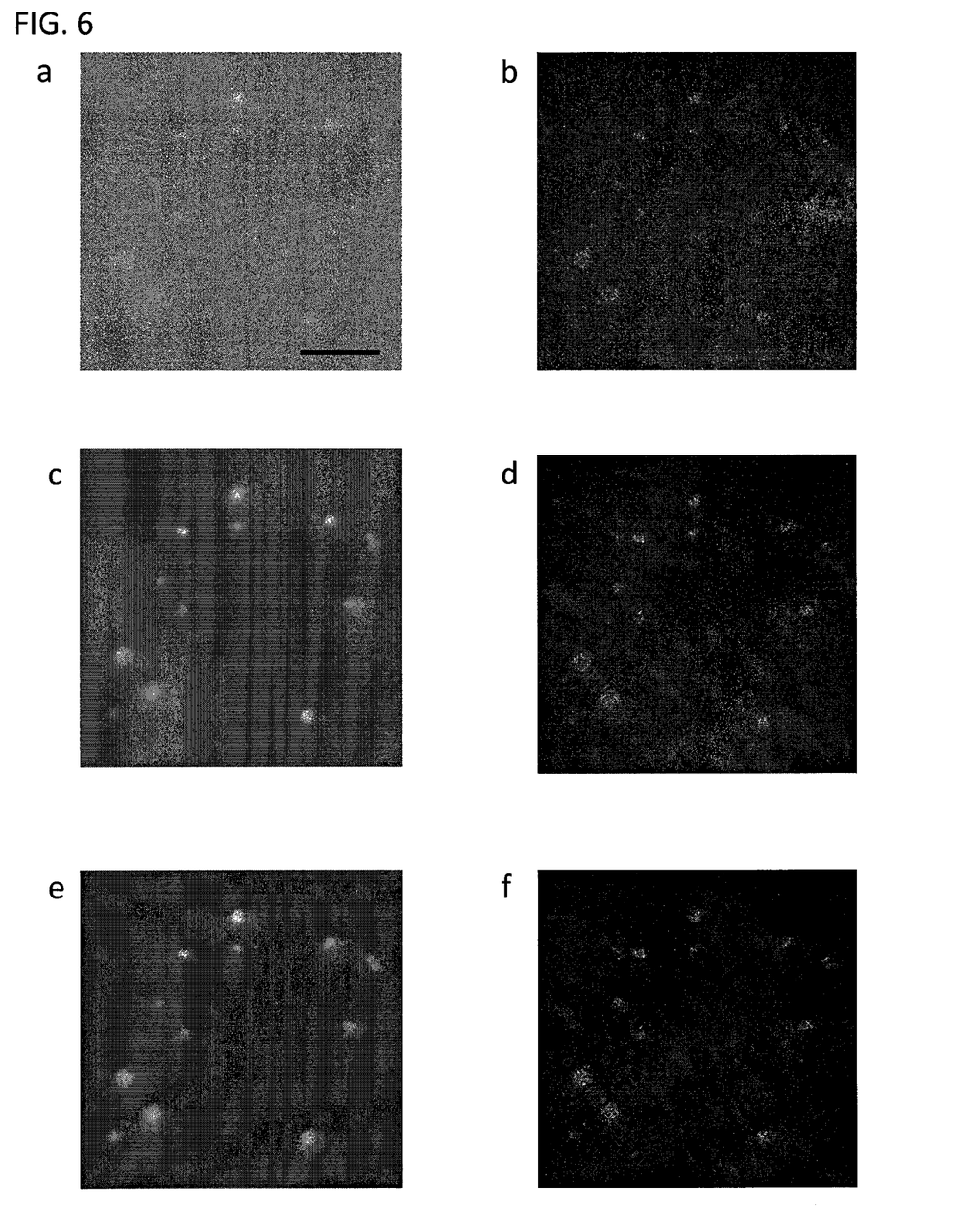
FIGS. 6a to 6f provide photographic and reconstructed holographic data images taken using an exemplary harmonic holography instrument in accordance with the current invention.

To compare the performance of direct and holographic imaging, direct and holographic images were captured under identical conditions at integrations of 1, 5, and 10 pulses, these are shown in FIG. 6. The experiments at different integration time are used to investigate the imaging characteristics as a function of signal intensity rather than the integration time itself. The femtosecond laser pulses exclude the use of spatial filters and result in imperfections in the reference. Consequently, although the axial location (z-coordinate) of the sample is accurately measured, it is necessary to numerically reconstruct a stack of images along z-axis within a 20 µm range to find the best focus (location with the highest image intensity) for the holographic reconstruction.

Because of the large dynamic range, the as-is image reconstructed from the hologram cannot be visualized with necessary clarity. Thus for visualization purpose, every picture is histogram-stretched in FIG. 6 so that the darkest 0.01% pixels are black and the brightest 0.01% pixels are white. The effect of aberration compensation is clearly visible, as the nebulous images in the direct picture become much sharper in the reconstructed holographic image, revealing the fine structure of the nanocrystal clusters through random phase-matching effect.

Figure 7:
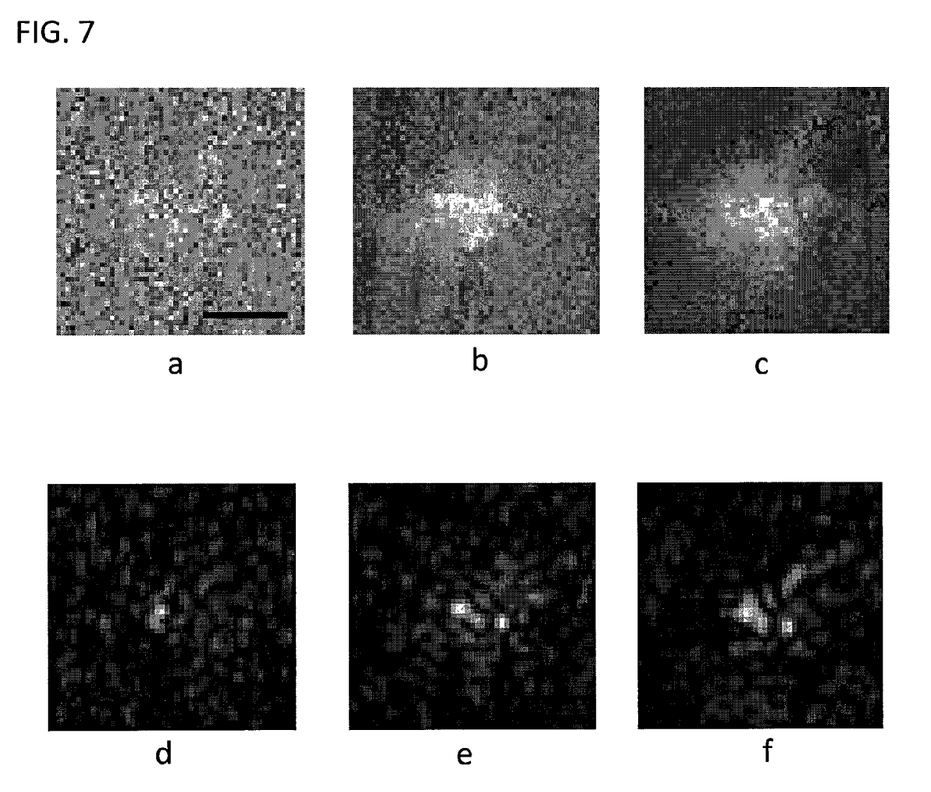
FIGS. 7a to 7f provide photographic and reconstructed holographic data images taken using an exemplary harmonic holography instrument in accordance with the current invention.

FIG. 7 shows a magnified image of object #7, which is the smallest object among all identified objects. The remarkable compactness of the images in FIGS. 7d to f suggests that the reconstruction is true focal images instead of speckles from off-focus objects. FIG. 7 also shows a clear gain in SNR through reference biasing and aberration compensation.

Figure 8:
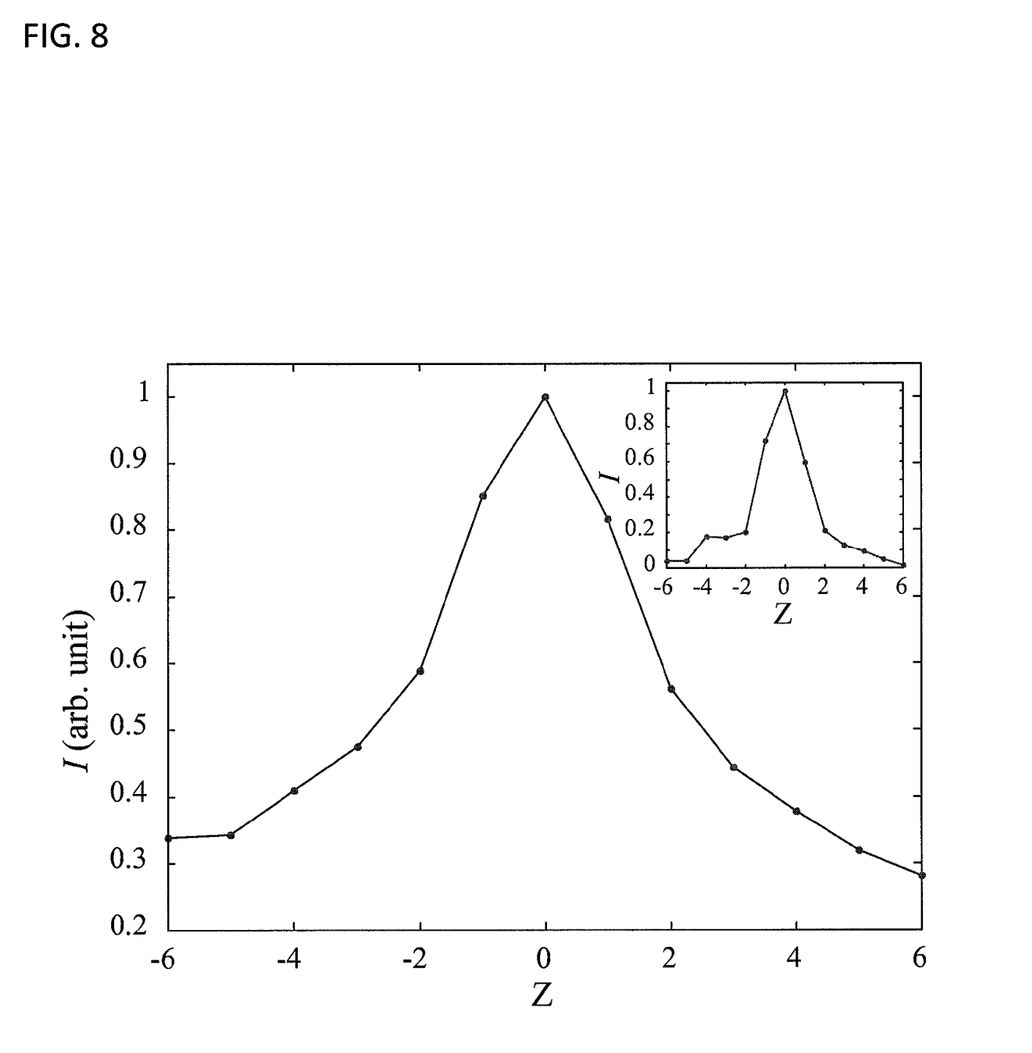
FIG. 8 provides data graphs taken using an exemplary harmonic holography instrument in accordance with the current invention.

Walking through the reconstructed image stack along z-axis reveals the axial intensity profile of the holographic reconstruction, which is plotted in FIG. 8. The plot was obtained by averaging the normalized image intensity as a function of z-coordinate over 50 randomly picked bright pixels at local maxima in FIG. 6f. The position at which FIG. 6f is obtained is set to z=0. The inset in FIG. 8 shows a plot for a typical individual intensity profile. FIG. 8 confirms that the images shown in FIG. 6 are true focal images. On average, the depth-of-focus of the reconstructed images is approximately 4.5 µm. The depth-of-focus of an individual, small object is roughly 2.5 µm. Because of the size of the nanocrystal clusters (several microns), individual profiles peak at slightly different z-coordinate, resulting in a broadened mean intensity profile.

Because of the obvious difficulty in defining an image center for each object, the signal intensity for every image spot may be defined as the mean intensity for pixels with intensity above 50% of the local intensity maximum. As stated previously, to minimize the influence of the shot noise and obtain accurate measurement, this procedure is performed only on an image of 100-pulse integration, and the intensity is then linearly scaled back to the proper integration of 1, 5, and 10 pulses. This approach is applied to both direct and holographic images to obtain signal intensities $\langle I_i^{(D)} \rangle$, and $\langle I_i^{(H)} \rangle$, respectively, where the equation:

$$\langle I_i^{(H)} \rangle = \langle Q_i^{(H)} \rangle / I_R \quad \text{(Eq. 3)}$$

is calculated from the mean intensity $\langle Q_i^{(H)} \rangle$, directly recovered from the hologram recorded with reference intensity $I_R$.

The gain of signal intensity can be quantified from aberration compensation, by a joint approach of ray tracing and wave propagation in the Fresnel regime in accordance with:

$$\gamma = \langle I_i^{(H)} \rangle / \langle I_i^{(D)} \rangle \quad \text{(Eq. 4)}$$

The value of γ is a function of the objective NA, since a larger NA results in higher aberrations and thus a higher gain when the aberration is canceled. In this particular configuration where an NA of 0.45 is achieved (limited by the size of the objective), numerical investigations show that the gain in signal intensity through aberration compensation is γ=1.63. If the objective NA is increased to 0.63 while all other parameters remain constant, the gain becomes γ=3.0.

Taking the shot noise into account, the SNR for the direct images can be defined as:

$$SNR^{(D)} = \frac{\langle I_i^{(D)} \rangle \cdot \Delta}{\sqrt{\langle I_i^{(D)} \rangle \cdot \Delta + (N^{(D)} \cdot \Delta)^2}},$$ (Eq. 5)

where $\Delta$ is the digitization sensitivity of the CCD camera in photons per digit, and $N^{(D)}$ is the device noise after digitization in the direct image. Here the impact of QE, which only affects the absolute sensitivity but not the SNR at the same level of $\langle I_i^{(D)} \rangle$, can be ignored. At the integration time used in this experiment, the read noise of the CCD camera dominates $N^{(D)}$.

The bias provided by the reference beam in $H^2$ renders the device noise negligible, and as such a shot noise-limited device is obtained for all signal levels. Therefore, the SNR for the holographic reconstruction is simply (again ignoring QE):

$$SNR^{(H)} = \sqrt{\langle I_i^{(H)} \rangle \cdot \Delta}.$$ (Eq. 6)

The overall gain in the SNR through holography over direct imaging is then:

$$G_{SNR} = \frac{SNR^{(H)}}{SNR^{(D)}} = \sqrt{\gamma}\left(1 + \frac{N^{(D)} \cdot \Delta}{\sqrt{I_i^{(D)}}}\right)$$ (Eq. 7)

Given that $\langle I_i^{(D)} \rangle \approx 2.5$ photons/pixel/pulse, $\Delta \approx 3$ photon/digit, and $N^{(D)} \approx 2.0$ in the camera used in this experiment, the measured SNR of the identified objects is listed in Table 1, below.

TABLE 1

SNR OF IDENTIFIED OBJECTS

| Exposure | | 1 | 2 | 3 | 4 | 5 | 6 | 7 | 8 | 9 | 10 | 11 |
|---|---|---|---|---|---|---|---|---|---|---|---|---|
| 1 Pulse | D | 1.1 | 1.2 | 0.9 | 1.1 | 0.9 | 1.4 | 1.0 | 1.2 | 1.2 | 1.0 | 0.9 |
| | H | 4.6 | 4.8 | 4.3 | 3.8 | 5.0 | 3.9 | 5.0 | 4.3 | 4.3 | 6.8 | 4.7 |
| 5 Pulses | D | 4.4 | 4.5 | 3.6 | 4.3 | 3.7 | 5.1 | 4.1 | 4.6 | 4.6 | 4.0 | 3.7 |
| | H | 9.5 | 10.0 | 8.8 | 7.8 | 10.3 | 8.1 | 10.4 | 8.8 | 8.9 | 14.1 | 9.7 |
| 10 Pulses | D | 7.0 | 7.3 | 6.0 | 7.0 | 6.0 | 8.2 | 6.6 | 7.4 | 7.5 | 6.5 | 6.1 |
| | H | 12.2 | 12.8 | 11.2 | 10.0 | 13.1 | 10.4 | 13.3 | 11.3 | 11.4 | 18.0 | 12.4 |

D: DIRECT IMAGING.
H: HOLOGRAPHIC RECONSTRUCTION.

Figure 9A:
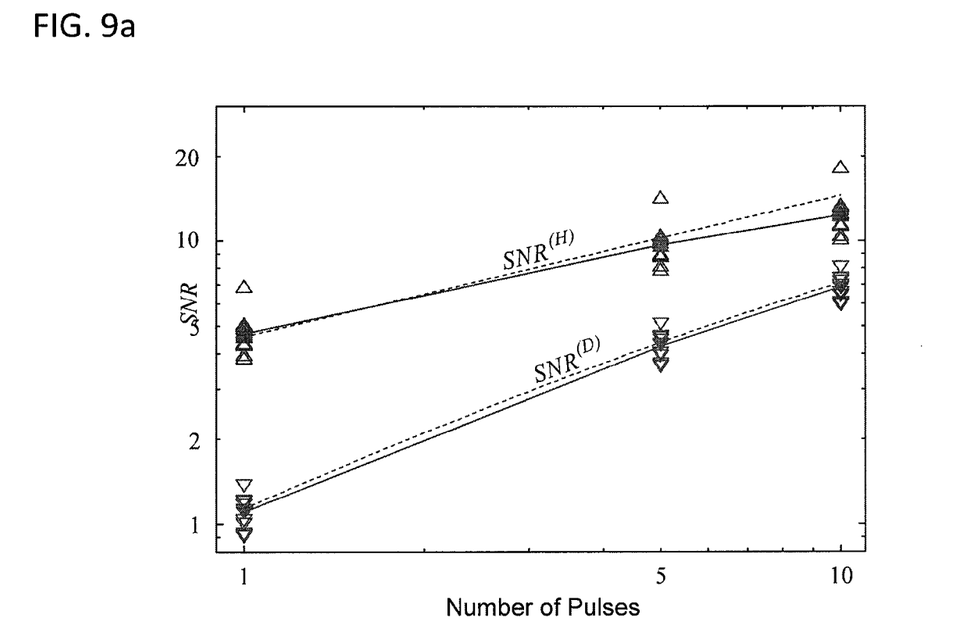
FIGS. 9a and 9b provide data graphs taken using an exemplary harmonic holography instrument in accordance with the current invention.
Figure 9B:
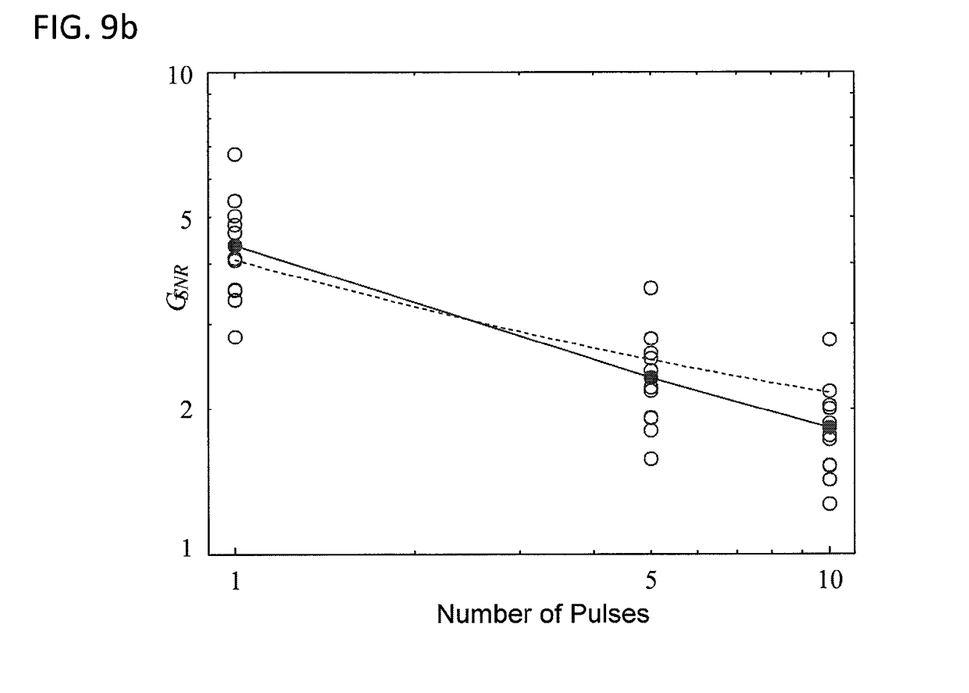

The fluctuations in $G_{SNR}$ for each individual object are a result of the extended object size, whose scattering wave front (at second harmonic frequency) deviates from that of a spherical wave. (See, e.g., Y. Pu and H. Meng, J. Opt. Soc. Am. A 20, 1920-1932 (2003), the disclosure of which is incorporated herein by reference.) In FIG. 9a, the SNR is plotted for both direct and holographic images, in red and blue respectively, as a function of the number of integrated pulses. The empty triangles represent the measured data points, solid triangles with lines show the mean values of the measurement, and the dashed lines are theoretical predictions from Equations 5 and 6, above. The gain in SNR, $G_{SNR}$, is plotted in FIG. 9b as a function of the number of integrated pulses, where empty circles are measurement data points, solid circles with line are the mean value, and the dashed line is the theoretical $G_{SNR}$ calculated from Equation 7, above. Due to the uncontrolled air flow in the lab environment, the value of $G_{SNR}$ at longer integration slightly falls below what is predicted by Equation 7.

SUMMARY

The current harmonic holography ($H^2$) technique provides a unique means to achieve contrast in the coherent domain, enabling the use of holography in ultrafast four-dimensional contrast imaging with high spatial and temporal resolution. The $H^2$ technique of the current invention records holograms using second harmonic signals scattered from SHG nanocrystals and an independently generated second harmonic reference. Exemplary experiments show that the technique of $H^2$ has unique advantages over direct imaging, including numerical aberration compensation and device noise canceling. In short, the $H^2$ technique of the current invention has proven to be a powerful technique to achieve aberration-free, shot noise-limited performance with low photon count signals, providing a technique that allows for molecular biomedical imaging applications.

While the above description contains many specific embodiments of the invention, these should not be construed as limitations on the scope of the invention, but rather as an example of one embodiment thereof. For example, although the optimal performance can be achieved through the use of high NA objectives (which bear significant aberrations when used to image a volume) and small pixel, fast frame rate cameras (which typically have high device noise), other detection and optical schemes may be used. Moreover, the principle of this technique is not limited to simple second harmonic signals, but can be extended to use other coherent optical process, such as sum frequency generation, difference frequency generation, and coherent anti-stokes Raman scattering providing even greater application flexibility. Accordingly, the scope of the invention should be determined not by the embodiments illustrated, but by the appended claims and their equivalents.

What is claimed is:
1. A nonlinear holographic imaging system comprising:
an excitation source for generating at least one optical puke;
a first optical splitter for separating said at least one optical pulse into at least one excitation puke and at least one reference pulse;

a sample optically aligned with said first optical splitter and comprising a target of interest having at least one nanoparticle incorporated therein, said at least one nanoparticle generating at least one coherent nonlinear harmonic optical emission when radiated by the at least one excitation pulse;

an optical filter in alignment with the sample for blocking all emissions from said sample except the at least one nonlinear harmonic emission;

a nonlinear homodyne reference generator in optical alignment with said first optical splitter for converting said at least one reference pulse into at least one coherent nonlinear harmonic reference pulse;

a second optical splitter in optical alignment with said reference generator and said filter such that the each of the at least one nonlinear harmonic reference pulse and the at least one nonlinear harmonic emission are recombined into at least one holographic signal; and a detector in optical alignment with said second optical splitter for recording said at least one holographic signal.

2. The nonlinear holographic imaging system of claim 1, wherein a single excitation puke is used.

3. The nonlinear holographic imaging system of claim 1, further comprising a computer algorithm to process the hologram recorded on the detector and reconstruct the images of said nanoparticles.

4. The nonlinear holographic imaging system of claim 3, further comprising obtaining images of the at least one nanoparticles on multiple planes.

5. The nonlinear holographic imaging system of claim 1, further comprising repeating said recording over time to obtain dynamic imaging of a process of interest.

6. The nonlinear holographic imaging system of claim 1, wherein the at least one nanoparticle is a second harmonic generating nanocrystal.

7. The nonlinear holographic imaging system of claim 6, wherein the at least one nanocrystal is selected from the group consisting of $BaTiO_3$, SiC, ZnO, ZnS, ZnSe, ZnTe, CdS, CdSe, Cite, GaAs, GaSb, GaP, GaN, InSb, $LiNbO_3$, $KnbO_3$, $KTiOPO_4$, $Fe(IO_3)_3$, Au, Ag, N-(4-nitrophenyl)-(L)-prolinol (NPP), 4-Nitroaniline, 2-Methyl-4-nitroaniline (MNA), and 3-Methyl-4-methoxy-4'-nitrostilbene.

8. The nonlinear holographic imaging system of claim 1, wherein the at least one nanoparticle is functionalized to attach to a specific target of interest.

9. The nonlinear imaging system of claim 1, wherein the target of interest is a bionnolecule selected from the group consisting of proteins, polypeptides, Danas, RNAs, nucleotides, neocleosides, lipids, ligands, receptors, and ion channels.

10. The nonlinear imaging system of claim 1, wherein the target of interest is a nnicrofluidic device.

11. The nonlinear imaging system of claim 1, wherein the sample comprises a three dimensional media.

12. The nonlinear imaging system of claim 1, further comprising a plurality of additional optical conditioning devices selected from the group consisting of mirrors, negative lenses, positive lenses, aspheric lenses, filters, optical splitters, and objectives.

13. The nonlinear imaging system of claim 1, wherein the nonlinear homodyne reference generator is a frequency doubler.

14. The nonlinear imaging system of claim 1, wherein the nonlinear emission is produced by a process selected from the group consisting of second harmonic generation, third harmonic generation, fourth harmonic generation, sum frequency generation, difference frequency generation, optical parametric down conversion, stimulated Raman scattering, coherent anti-Stokes Raman scattering, and surface-enhanced Raman scattering.

15. A holographic imaging system comprising:
an excitation source for generating broadband optical pulses;

a first optical splitter for separating said optical pukes into illumination pukes and reference pukes;

a sample optically aligned with said first optical splitter and comprising a target of interest having at least two metal nanoparticles incorporated therein, wherein when illuminated by the illumination pulses the at least two metal nanoparticles produce different absorption spectrum transmissions as a result of a collective plasmon resonance phenomenon dependent on the relative distance between the at least two metal nanoparticles;

a second optical splitter in optical alignment with said reference pulses and said sample such that the reference pulses and the transmissions from the sample are recombined into a holographic signal;

a second optical filter in alignment with said holographic signal for blocking all holographic signals except the holographic signal at a frequency of interest; and a detector in optical alignment with said second optical filter for recording said holographic signal.

16. The holographic imaging system of claim 15, wherein the target of interest moves the at least two metal nanoparticles between at least two states wherein the relative distance between the at least two metal nanoparticles changes to produce at least two different absorption spectrum; and wherein the detector records said holographic signal of said at least two states in rapid succession.

17. The holographic imaging system of claim 16, further comprising a computer algorithm to calculate the image of absorption difference between said first and second state at said frequency of interest from said holographic signal.

18. The holographic imaging system of claim 16, further comprising obtaining difference images between said at least two states on multiple planes.

19. The holographic imaging system of claim 15, further comprising repeating said recording over time to obtain dynamic imaging of a process of interest.

20. The holographic imaging system of claim 15, wherein the at least two metal nanoparticles are selected from the group consisting of Au, Ag, Al, Cu, Pd, and Pt.

21. The holographic imaging system of claim 15, wherein the at least two metal nanoparticles are functionalized to attach to a specific target of interest.

22. A method of producing holograms comprising:
providing a sample comprising a target of interest;
introducing at least one nanoparticle into said sample, said nanoparticle generating a coherent nonlinear emission when excited;
generating at least one energetic optical pulse from an excitation source;
splitting each of said at least one pulses into an excitation pulse and a reference pulse;
exciting said at least one nanoparticle in said sample with said excitation pulse such that the at least one nanoparticle generates at least one coherent nonlinear harmonic emission;
filtering the emission from said sample such that all emissions from said sample except the nonlinear emissions are blocked;
converting said reference pulse into a coherent nonlinear harmonic reference pulse;

combining the nonlinear harmonic reference puke and the nonlinear harmonic emission into a holographic signal; and recording said holographic signal.

23. The method of claim 22, wherein a single excitation puke is used.

24. The method of claim 22, further comprising processing the hologram recorded on the said detector and reconstructing the images of said at least one nanoparticle.

25. The method of claim 24, further comprising obtaining images of the said at least one nanoparticle on multiple planes.

26. The method of claim 22, further comprising repeating said recording over time to obtain dynamic imaging of a process of interest.

27. The method of claim 22, wherein the at least one nanoparticle is a second harmonic generating nanocrystal.

28. The method of claim 27, wherein at least one nanocrystal is selected from the group consisting of $BaTiO_3$, SiC, ZnO, ZnS, ZnSe, ZnTe, Cads, CdSe, Cite, GaAs, GaSb, GaP, GaN, InSb, $LiNbO_3$, $KnbO_3$, $KTiOPO_4$, $Fe(IO_3)_3$, Au, Ag, N-(4-nitrophenyl)-(L)-prolinol (NPP), 4-Nitroaniline, 2-Methyl-4-nitroaniline (MNA), and 3-Methyl-4-methoxy-4'-nitrostilbene.

29. The method of claim 22, wherein the at least one nanoparticle is functionalized to attach to a specific target of interest.

30. The method of claim 22, wherein the bionnolecule is selected from the group consisting of proteins, polypeptides, Danas, RNAs, nucleotides, neocleosides, lipids, ligands, receptors, and ion channels.

31. The method of claim 22, wherein the target of interest is a nnicrofluidic device.

32. The method of claim 22, wherein the sample comprises a three dimensional media.

33. The method of claim 22, further comprising a plurality of additional optical conditioning devices selected from the group consisting of mirrors, negative lenses, positive lenses, aspheric lenses, filters, optical splitters, and objectives.

34. The method of claim 22, wherein the nonlinear homodyne reference generator is a frequency doubler.

35. The method of claim 22, wherein the nonlinear emission is produced by a process selected from the group consisting of second harmonic generation, third harmonic generation, fourth harmonic generation, sum frequency generation, difference frequency generation, optical parametric down conversion, stimulated Raman scattering, coherent anti-Stokes Raman scattering, and surface-enhanced Raman scattering.

* * * * *